United States Patent
Zhang et al.

[11] Patent Number: 5,953,440
[45] Date of Patent: Sep. 14, 1999

[54] METHOD OF MEASURING THE FOCUS OF CLOSE-UP IMAGES OF EYES

[75] Inventors: Guang Hua Zhang, Maple Shade, N.J.; Marcos Salganicoff, Philadephia, Pa.

[73] Assignee: Sensar, Inc., Moorestown, N.J.

[21] Appl. No.: 08/982,364

[22] Filed: Dec. 2, 1997

[51] Int. Cl.⁶ .............................. G06K 9/00; G06K 9/48; G06K 9/40
[52] U.S. Cl. ..................... 382/117; 382/199; 382/255
[58] Field of Search ................................... 382/255, 200, 382/266, 199, 205, 272, 117; 348/345–354, 400–409

[56] References Cited

U.S. PATENT DOCUMENTS

| | | | |
|---|---|---|---|
| 5,534,923 | 7/1996 | Suda | 348/354 |
| 5,621,822 | 4/1997 | Yukawa et al. | 382/255 |
| 5,659,812 | 8/1997 | Uchiyama | 396/104 |
| 5,678,097 | 10/1997 | Suda | 396/113 |

*Primary Examiner*—Leo H. Boudreau
*Assistant Examiner*—Shawn B. Cage
*Attorney, Agent, or Firm*—Buchanan Ingersoll, P.C.

[57] ABSTRACT

In a method of determining whether an image of an eye is in focus a set of pixels is selected along a line passing through the pupil/iris boundary such that the set contains at least 5 iris portion pixels and at least 5 pupil portion pixels. Statistical values, preferably median values, are computed for all iris pixels in the selected set and for all pupil pixels in the selected set. The step size between the iris pixels and the pupil pixels is computed and absolute gradient values are computed for each pixel. The pixel having a largest absolute gradient value is excluded and an average of the absolute gradient values of the remaining pixels is found. If that average divided by the step size is greater than 0.5 the image is in focus and can be used for identifying a subject whose eye is in the image using iris identification techniques.

12 Claims, 2 Drawing Sheets

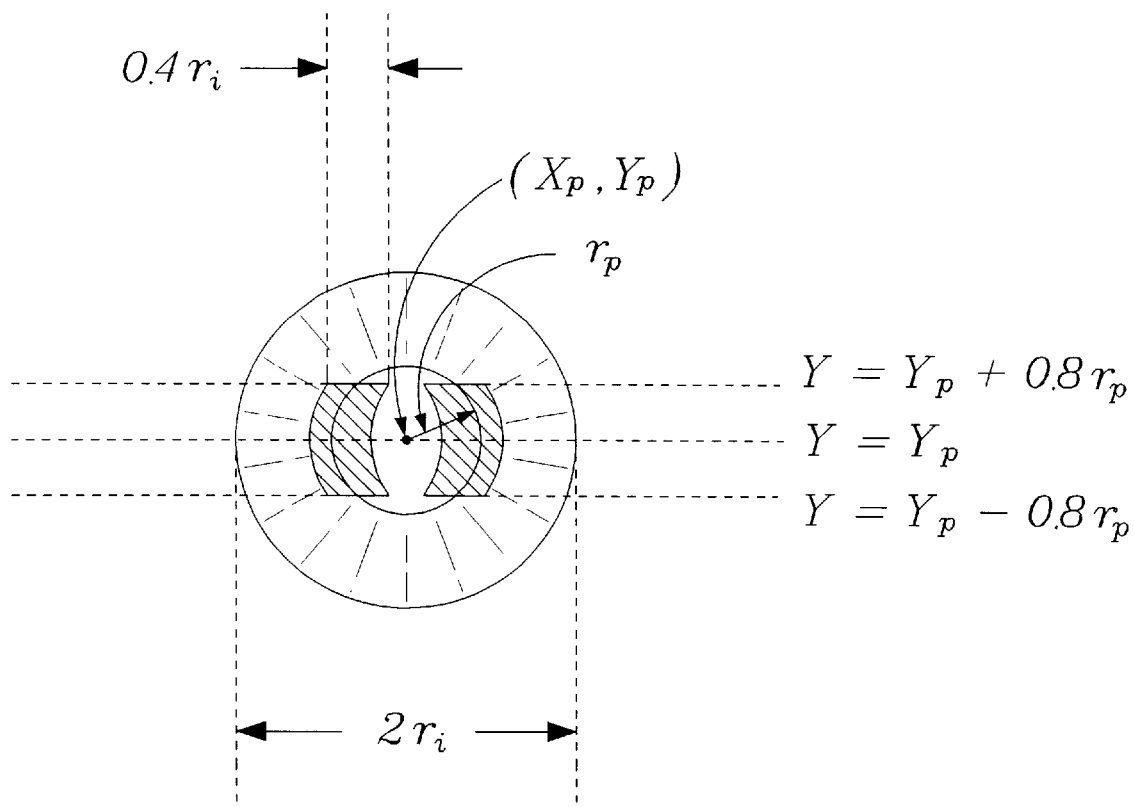

METHOD OF MEASURING THE FOCUS OF CLOSE-UP IMAGES OF EYES

FIELD OF THE INVENTION

The invention relates to identifying individuals from facial images, and more particularly from images of the eye.

BACKGROUND OF THE INVENTION

There are several methods known as biometrics for recognizing or identifying an individual from personal biological characteristics. Some of these methods involve imaging of the face or eye and analyzing the facial features, retinal vascular patterns of the eye, or patterns in the iris of the eye. In recent years there has been a demand for more reliable systems to identify individuals, particularly those persons who desire access to a secured area or system. A common example of such a secured system are automated teller machines which allow authorized users to conduct banking transactions. Many of these systems are used by a wide variety of people. Very often these people demand quick as well as accurate identification.

A technique for accurately identifying individuals using iris recognition is described in U.S. Pat. No. 4,641,349 to Flom et al. and in U.S. Pat. No. 5,291,560 to Daugman. The systems described in these references require clear, well-focused images of the eye. The present invention relates to assuring good focus in an image to be used in such systems.

SUMMARY OF THE INVENTION

We provide a reliable method for measuring the degree of focus in a close-up image of an eye. Given the approximate location of the pupil/iris boundary in the image, we measure how sharply this boundary is focused. We compute the median pixel value in a portion of the pupil, and then do the same for a portion of the iris. We subtract these medians to get the step size at the pupil/iris boundary. We compute the magnitude of gradients at the pupil/iris boundary. We divide an average of the gradient magnitudes by the step size to get the multiplicative inverse of the width of the transition region at the pupil/iris boundary. This latter value is maximum when the focus is optimized.

BRIEF DESCRIPTION OF THE FIGURES

FIG. 2 is an illustration of the selection of regions of an eye image to be used for calculating the degree of focus.

DESCRIPTION OF THE PREFERRED EMBODIMENTS

Figure 1:
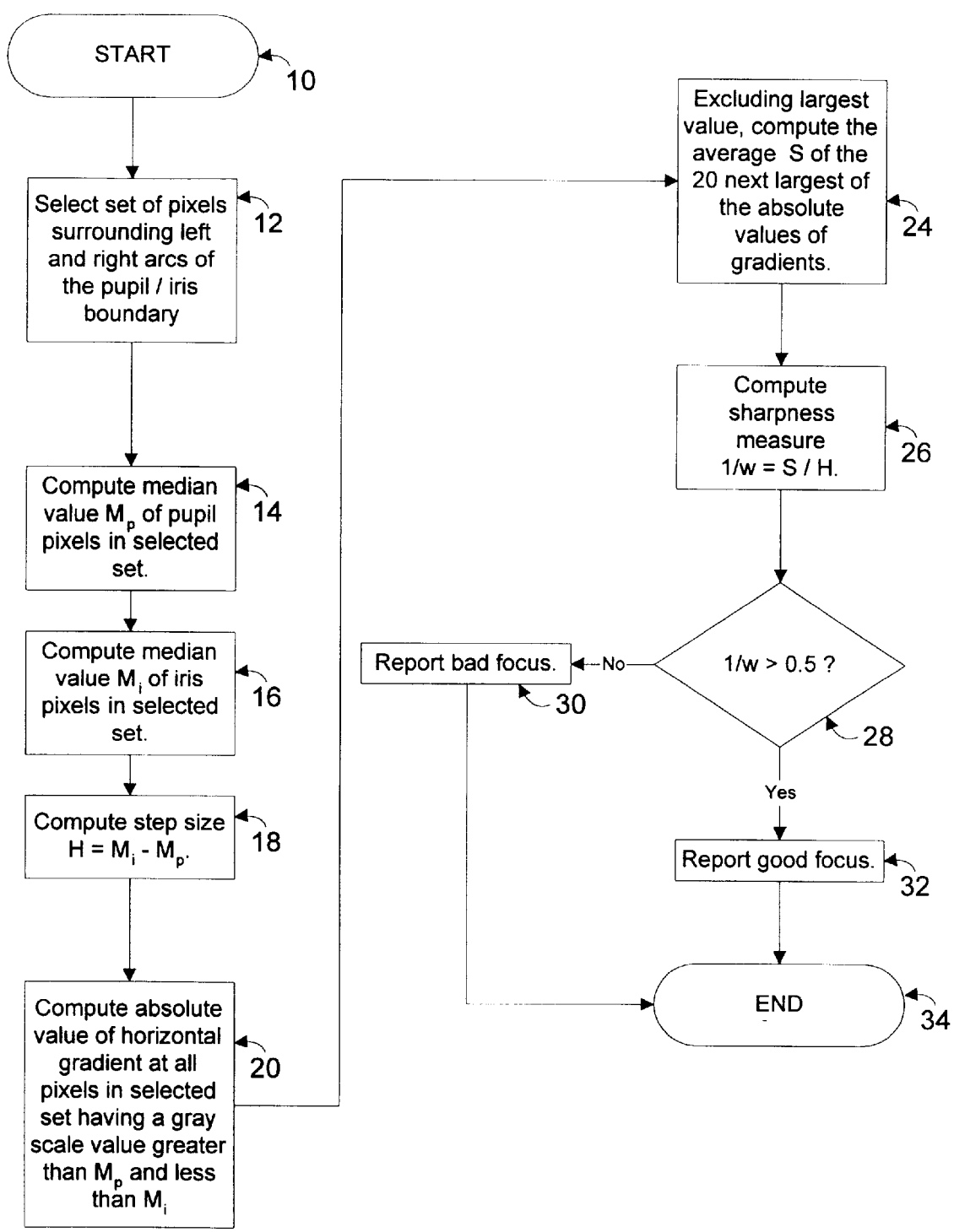
FIG. 1 is a flowchart of a preferred embodiment of the present invention.

Using a computer system with some standard video capture facility, such as a CCD video camera and video frame grabber, we obtain a close-up image of an eye. That image will be formed by a set of pixels each having a gray scale value. We then process this image according to the method of the present invention.

We begin at step 10 in FIG. 1 with a close-up image of an eye such as that shown in FIG. 2 and estimates of the location of the center of the pupil, $(x_p, y_p)$, the radius of the pupil, $r_p$, and the radius of the iris, $r_i$. (Note: x is the horizontal axis in the image and y is the vertical axis in the image.) It is also assumed that bright specular reflections in the image have been identified and that pixels contained in these specular reflections are excluded from subsequent calculations.

The image of the eye will contain an iris portion and a pupil portion. There is a boundary between the iris and the pupil. Since the pupil is dark and the region of the iris close to the pupil is much lighter, the sharpness of the pupil/iris boundary in the image will indicate if the image is in focus. At step 12, we select a set of pixels that is comprised of two regions that overlap the leftmost and rightmost portions of the pupil/iris boundary in the image for which the focus is to be measured. Each of the regions should contain a portion of the boundary that is at least 8–12 pixels long, and longer is better up to the point where the boundary may be occluded by eyelids or eyelashes. Each row of each region should contain at least 5 pupil pixels inside the boundary and at least 5 iris pixels outside the boundary. More pupil pixels may be used because the whole area of the pupil is generally quite uniform in intensity, but only iris pixels close to the boundary (less than about two-tenths of the iris radius from the center of the boundary) may be used because iris pixels farther from the boundary may have substantially different intensity.

In one preferred embodiment, the selected set of pixels near the pupil/iris boundary includes all pixels (x, y) such that $(y_p-0.8r_p)<y<(y_p+0.8r_p$ and $$(y_p - 0.8r_p) < y < (y_p + 0.8r_p \text{ and}$$

$$+\sqrt{r_p^2 - (y-y_p)^2} - 0.2r_i < x - x_p < +\sqrt{r_p^2 - (y-y_p)^2} + 0.2r_i$$

or $$-\sqrt{r_p^2 - (y-y_p)^2} - 0.2r_i < x - x_p < -\sqrt{r_p^2 - (y-y_p)^2} + 0.2r_i.$$

This set is graphically illustrated in FIG. 2. There is shown an iris 2 surrounding a pupil 4. The pupil has a radius $r_p$ and the iris has a radius $r_i$. The regions containing the selected set of pixels are cross hatched.

In step 14, we compute the median gray scale value of all pupil pixel gray scale values in the selected set to represent the overall intensity of the pupil image. For this calculation, pupil pixels are defined to be all pixels (x, y) such that $(y_p-0.8r_p)<y<(y_p+0.8r_p$ $$(y_p - 0.8r_p) < y < (y_p + 0.8r_p \text{ and}$$

$$+\sqrt{r_p^2 - (y-y_p)^2} - 0.2r_i < x - x_p < +\sqrt{r_p^2 - (y-y_p)^2} - 0.1r_i$$

or $$-\sqrt{r_p^2 - (y-y_p)^2} + 0.1r_i < x - x_p < -\sqrt{r_p^2 - (y-y_p)^2} + 0.2r_i.$$

Median is used instead of mean because it is less affected by a small number of non-pupil pixels that may be included in the estimated area of the pupil. In an alternative embodiment we can use the mean. We might also use more sophisticated statistical analysis of the pupil pixel values to get a statistical value representing overall pupil gray scale. For example, we might find the pixel value of the largest bin count of the largest peak in a smoothed histogram of pupil pixels, but median is adequate in many cases.

Similarly, in step 16, we compute the median of all iris pixel gray scale values in the selected set. For this calculation, iris pixels are defined to be all pixels (x, y) such that $$(y_p - 0.8r_p) < y < (y_p + 0.8r_p) \text{ and}$$

$$+\sqrt{r_p^2 - (y-y_p)^2} - 0.1r_i < -x_p < +\sqrt{r_p^2 - (y-y_p)^2} - 0.2r_i$$

or $$-\sqrt{r_p^2 - (y-y_p)^2} - 0.2r_i < x - x_p < -\sqrt{r_p^2 - (y-y_p)^2} - 0.1r_i.$$

As in step 14, the use of mean is also possible, and more sophisticated statistics may also be used.

In step 18, we compute the pixel value step size, H, across the pupil/iris boundary to be the iris pixel median value minus the pupil pixel median value.

As is well known to those skilled in the art, each pixel in an image has a gradient value which corresponds to the change in gray scale as compared to adjacent pixels. This value could be positive or negative. In step 20, we compute the absolute value of the gradient at those pixels in the selected set having a gray scale value greater than $M_p$ and less than $M_i$ using a small kernel, for example, a kernel of 3 or 5 pixels. We calculate gradient only at these boundary pixels because the gradient at pixels in the relatively uniform pupil and iris regions will be near zero. To get an estimate of the overall gradient at the boundary, we first reject the largest of the absolute values computed from the boundary pixels (in case some corruption such as a missed specular reflection has caused an outlying gradient value), and then average the next 20–30 largest absolute values (as indicated in step 24 of FIG. 1) to get S, a good estimate of the absolute value of the gradient at the pupil/iris boundary. For some images it may not be necessary to exclude the largest value.

We prefer to use the horizontal gradient in step 20 because it is easy to compute for the common rectangular pixel grid. The radial gradient would also work well, although it is more difficult to compute for a rectangular pixel grid.

Assuming that the gradient is constant through the transition region of the pupil/iris boundary, we have, by definition, S/H=1/w, where w is the effective width of the transition region (as shown in step 26 of FIG. 1). This positive quantity is a good measure of focus that is independent of image contrast, which affects the step size H. Since S, H, and w are all defined using discrete pixels as the measure of length, the quantity 1/w approaches 1 for the case of ideal focus when w=1 pixel. This ideal case can only occur if an extremely sharp, well-focused image of the pupil/iris boundary strikes an imager (for example, a CCD) exactly on the boundary between a dark pupil pixel and a lighter iris pixel at every point along the boundary image. In practice, the very sharp, but curved, boundary image must pass near the middle of some pixels. At these points, w=2 and 1/w=0.5. Thus, for the sharpest possible focus, 0.5<1/w<1.0. This knowledge is embodied in step 28 of FIG. 1 which decides whether an image has good focus (step 32) or bad focus (step 30), after which the new method is complete (step 34). In practice, the threshold 0.5 is selected empirically, because it depends on the quality of the optical system and the resolution of the imager. The preceding theoretical analysis would not hold if the optical system could not produce an image of the pupil/iris boundary sharp enough to pass through a single pixel at the imager. If we conclude that the image is in focus, we then accept the image for further processing. That further processing would include identifying the subject whose eye is in the image using iris identification techniques such as those disclosed in U.S. Pat. No. 4,641,349 to Flom et al. and in U.S. Pat. No. 5,291,560 to Daugman.

Although we have shown and described certain present preferred embodiments of our method it should be understood that our invention is not limited thereto but may be variously embodied within the scope of the following claims.

We claim:

1. A method of determining whether an image of an eye is in focus wherein the image contains an iris portion having a radius $r_i$ and a pupil portion having a radius $r_p$ and there is an pupil/iris boundary between the iris portion and the pupil portion, the image is formed of pixels and there are at least 5 pixels of the iris portion of the image and at least 5 pixels of the pupil portion of the image on a single line comprised of:

a. selecting a set of pixels along a line passing through the pupil/iris boundary the set containing at least 5 iris portion pixels and at least 5 pupil portion pixels:

b. computing a statistical value $M_i$ of all iris pixels in the selected set;

c. computing a statistical value $M_p$ of all pupil pixels in the selected set;

d. computing a step size H such that $H=M_i-M_p$;

e. determining a gradient of pixel values along the line for the selected set of pixels;

f. forming a second set of pixels by excluding from the selected set of pixels that pixel having a largest absolute gradient value;

g. determining an average S of the absolute gradient values of the pixels in the second set of pixels;

h. computing 1/w=S/H; and i. if 1/w is greater than 0.5 using the image for identifying a subject whose eye is in the image using iris identification techniques and if 1/w is less than or equal to 0.5 selecting a new image and repeating steps a through h.

2. The method of claim 1 wherein the set of pixels is along a radial line extending from a center of the pupil.

3. The method of claim 1 wherein the set of pixels is along a line extending horizontally across the image.

4. The method of claim 1 wherein the set of pixels is along a line extending vertically across the image.

5. The method of claim 1 wherein the statistical values $M_i$ and $M_p$ are median values.

6. The method of claim 1 wherein the statistical values $M_i$ and $M_p$ are mean values.

7. A method of determining whether an image of an eye is in focus wherein the image contains an iris portion having a radius $r_i$ and a pupil portion having a radius $r_p$ and there is an pupil/iris boundary between the iris portion and the pupil portion, the image is formed of pixels and there are at least 5 pixels of the iris portion of the image and at least 5 pixels of the pupil portion of the image on a single line comprised of:

a. selecting a set of pixels along a line passing through the pupil/iris boundary the set containing at least 5 iris portion pixels and at least 5 pupil portion pixels:

b. computing a statistical value $M_i$ of all iris pixels in the selected set;

c. computing a statistical value $M_p$ of all pupil pixels in the selected set;

d. computing a step size H such that $H=M_i-M_p$;

e. determining a gradient of pixel values along the line for the selected set of pixels;

f. determining an average S of the absolute gradient values of the pixels in the set of pixels;

g. computing $1/w = S/H$; and h. if $1/w$ is greater than 0.5 using the image for identifying a subject whose eye is in the image using iris identification techniques and if $1/w$ is less than or equal to 0.5 selecting a new image and repeating steps a through g.

8. The method of claim 7 wherein the set of pixels is along a radial line extending from a center of the pupil.

9. The method of claim 7 wherein the set of pixels is along a line extending horizontally across the image.

10. The method of claim 7 wherein the set of pixels is along a line extending vertically across the image.

11. The method of claim 7 wherein the statistical values $M_i$ and $M_p$ are median values.

12. The method of claim 7 wherein the statistical values $M_i$ and $M_p$ are mean values.

* * * * *